United States Patent [19]
Milne, Jr. et al.

[11] Patent Number: 5,270,323
[45] Date of Patent: Dec. 14, 1993

[54] METHOD OF TREATING IMPOTENCE

[75] Inventors: George M. Milne, Jr., Niantic, Conn.; Michael G. Wyllie, Canterbury, England

[73] Assignee: Pfizer Inc., New York, N.Y.

[21] Appl. No.: 31,047

[22] Filed: Mar. 11, 1993

Related U.S. Application Data

[63] Continuation of Ser. No. 531,494, May 31, 1990, abandoned.

[51] Int. Cl.$^5$ ............................................. A61K 31/47
[52] U.S. Cl. ..................................................... 514/309
[58] Field of Search ........................ 514/309, 254, 356

[56] References Cited

U.S. PATENT DOCUMENTS

| | | | |
|---|---|---|---|
| 4,127,118 | 11/1978 | Latorre | 128/79 |
| 4,188,390 | 2/1980 | Campbell | 424/251 |
| 4,510,157 | 4/1985 | Asselin et al. | 514/411 |
| 4,572,909 | 2/1986 | Campbell et al. | 514/356 |
| 4,686,228 | 8/1987 | Campbell et al. | 514/307 |
| 4,758,569 | 7/1988 | Swindell | 514/254 |
| 4,801,587 | 1/1989 | Voss et al. | 514/248 |
| 4,806,557 | 2/1989 | Campbell et al. | 514/356 |
| 4,879,303 | 11/1989 | Davison et al. | 514/356 |
| 4,925,837 | 5/1990 | Cavero et al. | 514/211 |

FOREIGN PATENT DOCUMENTS

| | | |
|---|---|---|
| 266968 | 11/1988 | European Pat. Off. |
| 62-175427 | 8/1987 | Japan |

OTHER PUBLICATIONS

Morales, et al., "Is Yohimbine Effective in the Treatment of Organic Impotence? Results of a Controlled Trial", The Journal of Urology 137: 1168–1172 (1987).

Bommer, et al., "Improved Sexual Function in Male Haemodialysis Patients on Bromocriptine", The Lancet, Sep. 8, 1979, pp. 496–497.

Antoniou, et al., "Reversal of Uraemic Impotence by Zinc", The Lancet, Oct. 29, 1977, pp. 895–898.

Mudd, John W., "Impotence Responsive to Glyceryl Trinitrate", Am. J. Psychiatry 134:8, Aug. 1977.

Brindley, G. S., "Pilot Experiments on the Actions of Drugs Injected Into the Human Corpus Cavernosum Penis", Br. J. Pharmac. 87: 495–500 (1986).

Rayner, et al., "Penile Erection Due to Nifedipine", Brit. Med. J. 296: 137 (1988).

R. R. Luther, Am. J. Hypertension, vol. 2, No. 9, pp. 729–735, Sep. 1989, The American Journal of Hypertension, Inc., "New perspectives on selective alpha 1 blockade".

F. Holmquist et. al., European Journal of Pharmacology, vol. 186, pp. 87–93, Sep. 1990, Elsevier Science Publishers B. V. (Biomedical Division) "Effect of the alpha 1-adrenoceptor antagonist R-(−)-YM126217 on isolated human penile erectile tissue and vas deferens".

H. Hedlund et. al., J. Autonon. Pharmacol., vol. 5, pp. 81–88, 1985, "Comparison of the responses to drugs acting on adrenoreceptors and muscarinic receptors in human isolated corpus cavernosum and cavernous artery".

Primary Examiner—Leonard Schenkman
Attorney, Agent, or Firm—Peter C. Richardson; Gregg C. Benson; A. Dean Olson

[57] ABSTRACT

A method of relieving erectile impotence in a human male. The method comprises administering to the male an erectile impotence relieving amount of a compound selected from the group consisting of U.K. 52,046, Amlodipine, Doxazosin and the pharmaceutically acceptable acid addition salts thereof.

7 Claims, No Drawings

METHOD OF TREATING IMPOTENCE

This is a continuation of application Ser. No. 07/531,494 filed on May 31, 1990, abandoned.

TECHNICAL FIELD

The field of art to which this invention pertains is methods of treating male erectile impotence and more particularly the use of erection enhancing compounds to treat male erectile impotence.

BACKGROUND ART

Impotence is the inability to obtain and sustain an erection sufficient for intercourse. The penis becomes erect when certain tissues (in particular, the corpora cavernosa) in the central portion of the penis becomes engorged with blood thereby causing them to become less flaccid, and in turn causing an erection. It is estimated that 10–12 million American men between the ages of 18 and 75 suffer from chronic impotence with the great majority being over the age of 55.

Impotence results from psychologic disturbances (psychogenic), from physiologic abnormalities (organic) or from a combination of both. Typically, multiple factors are responsible for impotence.

The major causes of organic impotence are vascular abnormalities, neurologic deficiencies and drug treatment side effects. The primary vascular causes of impotence are arterial insufficiency, which prevents the penis from filling with blood, and venous abnormalities that prevent the retention of blood in the penis during the erectile process. Arterial insufficiency is primarily due to atherosclerosis and has been found to be exacerbated by smoking. A less frequent and somewhat unlikely vascular cause of impotence is priapism, prolonged painful erection, which can cause hypoxia and death of penile tissue.

The search for impotence treatment methods has included external devices for example, tourniquets (see U.S. Pat. No. 2,818,855). In addition penile implants, such as hinged or solids rods and inflatable, spring driven or hydraulic models, have been used for some time. The administration of erection effecting and enhancing drugs is taught in U.S. Pat. No. 4,127,118. That patent teaches a method of treating male impotence by injecting into the penis an appropriate vasodilator, in particular, an adrenergic blocking agent or a smooth muscle relaxant to effect and enhance an erection. More recently U.S. Pat. No. 4,801,587 teaches the application of an ointment to relieve impotence. The ointment consists of the vasodilators papaverine, hydralazine, sodium nitroprusside, phenoxybenzamine, or phentolamine and a carrier to assist absorption of the primary agent through the skin. In addition, Yohimbine, an alpha adrenergic antagonist is currently marketed with the suggestion that it may be efficacious in treating psychogenic impotence.

Although the injection of such agents as papaverine into the corpora cavernosa has proven effective, typically large doses 8 to 32 mg are required, resulting in undesired side effects such as pain, priapism and tissue fibrosis. The other impotence relieving agents also have one or more of the above problems when administered intracavernosally.

Thus, there is a continuing search in this field of art for improved methods for relieving male erectile impotence.

SUMMARY OF THE INVENTION

The invention is directed to a method of relieving erectile impotence in a human male. The method comprises administering to the male an erectile impotence relieving amount of a compound selected from the group consisting of U.K. 52,046, Amlodipine, Doxazosin and the pharmaceutically acceptable acid addition salts thereof.

Other features and advantages will be apparent from the specification and claims.

DETAILED DESCRIPTION OF THE INVENTION

Doxazosin, which has the chemical structure:

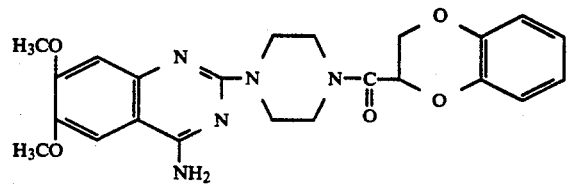

and its pharmaceutically acceptable acid addition salts are described in commonly assigned U.S. Pat. No. 4,188,390, entitled "Antihypertensive 4-Amino-2-[4(1,4-Benzodioxan-2-carbonyl)Piperazin-1-yl or Homopiperazin-1-yl]Quinazolines", the disclosure of which is hereby incorporated by reference. U.K.-52,046, which has the chemical structure

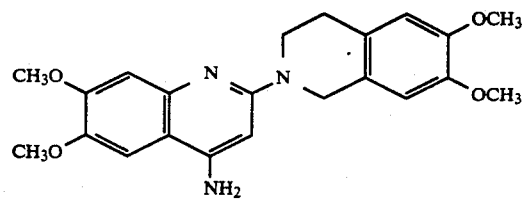

and its pharmaceutically acceptable acid addition salts are described in commonly assigned U.S. Pat. No. 4,686,228, entitled "Quinoline Therapeutic Agents", the disclosure of which is hereby incorporated by reference.

Amlodipine, which has the chemical structure

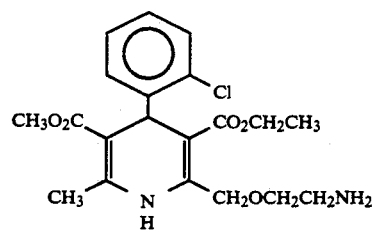

and its pharmaceutically acceptable acid addition salts are described in commonly assigned U.S. Pat. No. 4,572,909, entitled "2-(Secondary Aminoalkoxymethyl)Dihydropyridine Derivatives as Anti-Ischaemic And Antihypertensive Agents", the disclosure of which is hereby incorporated by reference.

Although the generic names Doxazosin, Amlodipine and U.K. 52,046 represent the free base, the present invention is also meant to embrace their pharmaceutically acceptable acid addition salts, such as hydrochloride, hydrobromide, hydroiodide, nitrate, sulfate, bisulfate, phosphate, acid phosphate, acetate, lactate, citrate, acid citrate, tartrate, bitartrate, salicylate, succinate, maleate, gluconate, methane sulfate, ethane sulfate, methane sulfonate (mesylate), benzenesulfonate (besylate), toluene sulfonate and p-toluenesulfonate salts. However preferred are the mesylate or besylate salts.

Any method of administration of the above compounds found effective in relieving male erectile impotence may be used. Preferably the administration is parenteral (e.g. injection, air gun) or transdermal (e.g. iontophoresis, passive transport) as these methods direct the compound to the critical tissues.

For purposes of parenteral administration, (e.g. intracavernosal) solutions of these particular compounds in sesame or peanut oil or in aqueous propylene glycol may be employed, as well as sterile aqueous solutions of the corresponding water soluble acid addition salts previously enumerated. Such aqueous solutions should be suitably buffered if necessary. These particular aqueous solutions are especially suitable for intracavernosal injection purposes. In this connection, the sterile aqueous media employed are readily obtained by standard techniques well known to those skilled in the art. For instance, distilled water is ordinarily used as the liquid diluent and the final preparation is passed through a suitable bacterial filter such as a sintered glass filter or a diatomaceous-earth or unglazed porcelain filter. Preferred filters of this type include the Berkefeld, the Chamberland and the Asbestos Disk-Metal Seitz filter, wherein the fluid is sucked into a sterile container with the aid of a suction pump. Needless to say, the necessary steps should be taken throughout the preparation of these injectable solutions to insure that the final products are obtained in a sterile condition. The injection can be made by needle or air gun. Typically the injection is made into the corpus cavernosum although any injection that is effective in relieving impotences may be used.

Any amount of the above described compounds when administered by injection that is effective in relieving male erectile impotence may be used. Because the compounds are vasodilators the drugs can reduce the blood pressure resulting in systemic cardiovascular effects (e.g. fainting). Thus, preferably the amount is below that amount which is the threshold limit for a significant systemic cardiovascular effect.

The frequency of delivery, of the amounts described below, relates to the frequency of impotence relief. Typically the compounds are administered just prior to the desire to obtain and sustain an erection. However as previously stated the total amount delivered is preferably below the threshold limit for significant systemic cardiovascular effects.

Preferably about 0.1 µg to about 25 µg U.K.-52,046 is used in a single dose. Preferably about 0.125 mg to about 5 mg Doxazosin is used in a single dose. Preferably about 0.125 mg to about 10 mg Amlodipine is used in a single dose.

Below the lower limit the compounds are not effective and above the upper limit significant systemic cardiovascular effects may occur.

The above described compounds can also be administered transdermally. For purposes of transdermal administration, the dosage from of the particular compound may include, by way of example, solutions, lotions, ointments, creams, gels, suppositories, rate-limiting sustained release formulations and devices therefor. Such dosage forms comprise the particular compound and may include ethanol, water, penetration enhancer and inert carriers such as gel-producing materials, mineral oil, emulsifying agents, benzyl alcohol and the like. Specific transdermal flux enhancing compositions are disclosed in commonly assigned co-pending U.S. patent application Ser. No. 925,641, the teachings of which are incorporated by reference. That specification teaches a transdermal flux composition comprising a pharmacologically active compound or a prodrug thereof, an aqueous ethanol solvent containing from 15% to 75% ethanol by volume and cis-olefin compounds such as oleic acid.

For transdermal administration the compounds may, for example, simply be applied directly to the penis. In another method of transdermal application the compounds may be delivered transdermally utilizing iontophoresis. In iontophoresis a drug is transported from a solution (disposed against the skin) across the dermal barrier by the application of a current across the solution and skin.

Any amount of the above described compounds when administered transdermally that is effective in relieving male erectile impotence may be used.

Typically the same amounts are preferably delivered to the critical tissues as are delivered by injection, however the amounts applied transdermally are typically greater because of the low effectiveness of transdermal administration for delivery to the critical tissues. As with injection, the amounts delivered are preferably below the threshold limit for significant systemic cardiovascular effects. The frequency of delivery is the same as described for injection. The amounts detailed below are for passive transdermal delivery. It is believed that for iontophoretic delivery the ranges would be reduced by a factor of 10 based on the greater efficiency of iontophoretic delivery.

Thus, preferably about 100 µg to about 100 mg U.K.-52,046 is used in a single dose. Preferably about 0.5 mg to about 500 mg Doxazosin is used in a single dose. Preferably about 20 mg to about 20 g Amlodipine is used in a single dose.

EXAMPLE 1

Seventeen mature adult male monkeys (age unknown) either Cercopithecus aethiops (green monkey) or Macaca fasciculata (cynomologous) weight range 4.7 to 7.1 kg were used. Animals were anaesthetised with diazepam (2.5 mg), ketamine chloride (20 µg/kg i.m. supplemented as appropriate) and given the appropriate drug dissolved in saline intracavernosally (0.3 ml). In a separate series of experiments to determine threshold effects, varying volumes of i.v. injectable solution were injected intracavernosally. Animals were placed supine, the penis stretched out and a rubber band placed around the root of the base as a tourniquet kept in place for three minutes after the injection. The solution was injected through a 27G needle into one of the corpus cavernosa and 5, 10, 25, 30, 60 and 180 minutes later tumescence (increase in volume) and rigidity of the penis was estimated visually and by palpitation. To determine the threshold effect using the injectable solution a series of animals were used covering an appropriate dose range, e.g., U.K. 52,046 (0.05 to 0.3 µg). The antidote/reversal experiments involved intracavernosal administration of noradrenaline (10 μg) phenylephrine (10 μg) or clonidine (15 μg).

Table 1 below details the comparative effect of U.K.-52,046, Doxazosin, Amlodipine, Papaverine and Phentolamine by injection to monkeys as described in Example 1 above. Surprisingly U.K.-52,046, Doxazosin, and Amlodipine all were effective for causing Tumescence and Rigidity at significantly lower doses than either Phentolamine or Papaverine. In fact, U.K.-52,046 was effective at doses 1000 times lower than for Phentolamine or Papaverine.

TABLE 1

Comparative Effects In Monkeys

| Drug | Threshold Dose | Tumescence | Rigidity | Time Course | Reversible |
|---|---|---|---|---|---|
| U.K.-52,046 | 0.1 μg | +++ | +++ | S | S |
| Doxazosin | 100 μg | ++ | + | S | S |
| Papaverine | 6.0 mg | ++ | ++ | S | S |
| Amlodipine | 500 μg | ++ | ++ | X | X |
| Phentolamine | 1.5 mg | ++ | ++ | S | S |

0 = no effect
+ = minimal effect
++ = good effect
+++ = full effect
S = satisfactory
X = unsatisfactory

EXAMPLE 2

Sheets of excised human skin cut to about 350 μm thickness were mounted between two halves of a diffusion cell (Side-by-Side, Crown Glass) with the stratum corneium side toward the donor compartment which contained 3 ml of radiolabelled drug in the appropriate vehicle. The receiver compartment contained 3 ml of 40% (v/v) ethanol in an acetate buffer. Both compartments were stirred with a magnetic stirrer and maintained at 32° C.

Samples were removed periodically from the receiver side of the diffusion cell, mixed with scintillation cocktail (Ecolume, ICN Radiochemicals) and counted for 10 minutes in a liquid scintillation counter (Tri-Carb 2000CA, Packard). Following an initial lag phase of several hours, the amount of radiolabeled drug appearing in the receiver side was linear with time for the duration of the experiment (routinely 24-48 hours). From a linear least squares analysis of these data the rate of appearance of UK-52,046 in the receiver chamber was determined. This value, when divided by the specific radioactivity of the drug in the donor solution and the area of exposed skin (1 cm$^2$), yielded the flux (μg/cm$^2$/hr). Samples removed from the donor chamber at the beginning and end of the experiment contained, within error, the same amount of UK-52,046. Thus, constant concentration of the permeant was maintained on the donor side throughout the experiment. Values for the delivery of UK-52,046 reflect total radioactivity; no measure of the amount of intact drug was made.

Table 2 below details the effective in vitro transport of UK-62,046 transdermally according to the procedure described in Example 2.

TABLE 2

Transport of U.K.-52,046 across human skin from a solution containing 8 mg/ml drug as the mesylate salt in 40% (v/v) ethanol:buffer (pH 4.5)

| Skin Type | Flux (μg/cm$^2$/h) | n |
|---|---|---|
| Thigh | 3.25 | 1 |
| Thigh | 3.53 | 1 |
| Thigh | 1.69 | 1 |
| Thigh | 0.95 | 3 |
|  | x = 1.98 ± 0.96 |  |
| Penis | 0.63 | 2 |

Table 3 expands on Table 2 above by using a pretreatment to enhance the effective transdermal in vitro transport of UK-52,046. The procedure used was according to Example 2.

TABLE 3

In vitro transport of UK-52,046 across human cadaver skin as a function of various pre-treatments. The vehicle was 40% (v/v) ethanol:buffer (pH 4.5).

| Treatment[2] | Flux[1] (μg/cm$^2$/h) |
|---|---|
| No pre-treatment | 0.95 |
| Vehicle, no Oleic | 0.22 |
| Vehicle + 0.25% Oleic Acid | 1.26 |
| 100% Oleic Acid | 2.45 |

[1]All values are the mean of three replicates.
[2]Treatment was for 3 hours prior to the diffusion study. A concentration of 8 mg/ml UK-52,046 was employed.

This invention provides methods of treating male erectile impotence by the administration of certain compounds to effect and enhance an erection. These compounds are effective at very low dosages and thus reduce the undesired side effects of other compounds.

It should be understood that the invention is not limited to the particular embodiments shown and described herein, but that various changes and modifications may be made without department from the spirit and scope of this novel concept as defined by the following claims.

We claim:

1. A method of relieving erectile impotence in a human male comprising administering to said male an erectile impotence relieving amount of the compound U.K.-52,046 and the pharmaceutically acceptable acid addition salts thereof.

2. The method as recited in claim 1 wherein the compound is the mesylate salt.

3. The method as recited in claim 1 wherein the compound is administered by injection.

4. The method as recited in claim 1 wherein the compound is administered transdermally.

5. The method as recited in claim 2 wherein a single dosage is about 0.1 μg to about 25 μg.

6. The method as recited in claim 3 wherein a single dosage is about 10 μg to about 100 mg.

7. The method as recited in claim 1 wherein the compound is the methane sulfonate salt of U.K. 52,046.

* * * * *